(12) United States Patent
Schmidt et al.

(10) Patent No.: US 7,034,107 B2
(45) Date of Patent: Apr. 25, 2006

(54) HIGH THROUGHPUT ASSAYS FOR THE PROTEOLYTIC ACTIVITIES OF CLOSTRIDIAL NEUROTOXINS

(75) Inventors: James J. Schmidt, Mt. Airy, MD (US); Robert G. Stafford, Ranson, WV (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/802,574

(22) Filed: Mar. 17, 2004

(65) Prior Publication Data

US 2004/0146963 A1    Jul. 29, 2004

Related U.S. Application Data

(63) Continuation of application No. 09/962,360, filed on Sep. 25, 2001, now Pat. No. 6,762,280.

(60) Provisional application No. 60/235,050, filed on Sep. 25, 2000.

(51) Int. Cl.
*C07K 14/00* (2006.01)
*A61K 39/08* (2006.01)

(52) U.S. Cl. .............. 530/300; 530/324; 530/333; 530/344; 530/350; 424/239.1; 435/4; 435/7.71; 435/7.72; 435/219

(58) Field of Classification Search ........... 530/300, 530/326, 324, 333, 335, 337, 344, 345, 350; 514/2, 13; 435/4, 7.71, 7.72, 252.7, 842, 435/183, 219; 930/10, 20; 424/239.1
See application file for complete search history.

(56) References Cited

U.S. PATENT DOCUMENTS 5,605,809 A    2/1997   Packard et al.
5,965,699 A    10/1999  Bostian et al.

FOREIGN PATENT DOCUMENTS

WO    WO 95/33850    * 12/1995
WO    WO0192312       12/2001

OTHER PUBLICATIONS

Soleilhac et al. (1996) A sensitive and rapid fluoresence-based assay for determination of tetanus toxin peptidase activity. Analytical Biochemistry 241, 120-127.
Anne, C. et al. (2001) High-throughput fluorogenic assay for determination of botulinum type B neurotoxin protease activity. Analytical Biochemistry 291, 253-261.
Roques, B. P. et al. (2000) Mechanism of action of clostridial neurotoxins and rational inhibitor design. Biology of the Cell 92, 445-557.

* cited by examiner

*Primary Examiner*—Kathleen M. Kerr
*Assistant Examiner*—Chih-Min Kam
(74) *Attorney, Agent, or Firm*—Elizabeth Arwine

(57) ABSTRACT

In this application is described substrates for high-throughput assays of clostridial neurotoxin proteolytic activities. Two types of substrates are described for use in assays for the proteolytic activities of clostridial neurotoxins: (1) modified peptides or proteins that can serve as FRET substrates and (2) modified peptides or proteins that can serve as immobilized substrates. In both types a fluorescent molecules is present in the substrate, eliminating the requirement for the addition of a fluorigenic reagent. The assays described can be readily adapted for use in automated or robotic systems.

9 Claims, 3 Drawing Sheets

FIG. 2b

Figure 2b: Per Cent of maximum Fluorescence vs. Toxin (μg/ml) for Type D (filled squares) and Type F (open circles).

HIGH THROUGHPUT ASSAYS FOR THE PROTEOLYTIC ACTIVITIES OF CLOSTRIDIAL NEUROTOXINS

This application is a Continuation of U.S. patent application Ser. No. 09/962,360, filed Sep. 25, 2001, now U.S. Pat No. 6,762,280, which claims benefit of U.S. Provisional Application No. 60/235,050, filed Sep. 25, 2000.

INTRODUCTION

The clostridial neurotoxins consist of tetanus toxin and the seven immunologically distinct serotypes of botulinum neurotoxin, elaborated by various strains of *Clostridium tetani* and *Clostridium botulinum*, respectively. They are among the most potent toxins known [Simpson, L. L. (1986) Ann. Rev. Pharmacol. Toxicol. 26: 427–453; Nieman, D. H. (1991) In: Sourcebook of Bacterial Protein Toxins (J. Alouf and J. Freer, Eds.) pp 303–348, Academic press, New York]. All references cited herein supra and infra are hereby incorporated in their entirety by reference thereto.

Nonetheless, these toxins have proven to be highly useful tools for research on the mechanisms of neurotransmitter release [Nieman, D. H. (1991) Trends Cell Biol. 4: 179–185; Schiavo, et al. (1994) Cell Biol. 5: 221–229], and are being used as clinical drugs in humans to treat a rapidly expanding group of muscle dysfunctions including strabismus, blepharospasm, cervical dystonia, and hemifacial spasm [Jancovic and Brin (1992) New Engl. J. Med. 324: 1186–1194; Kessler and Benecke (1997) Neurotoxicology 18(3): 761–770]. Although accidental botulinum intoxication is not considered a major public health threat, clostridial neurotoxins have long been recognized as potential biowarfare or bioterrorist agents [Arnon, S. S., et al. (2001) JAMA 285: 1059–1070].

The clostridial neurotoxins are synthesized by the bacteria as single-chain proteins of Mr ~150,000, which are subsequently cleaved by endogenous proteases to yield a light chain (Mr ~50,000) and a heavy chain (Mr ~100,000), covalently linked to each other by a disulfide bond [Bandyopadhyay, et al. (1987) J. Biol. Chem. 262: 2660–2663]. The heavy chains contain receptor-binding and translocation domains, required for entry of neurotoxin into target cells. The light chains are zinc metalloproteases, highly specific for certain proteins involved in neurotransmitter release [Montecucco and Schiavo (1994) Mol. Microbiol. 13: 1–8]. Botulinum serotypes A and E cleave the protein SNAP-25, while tetanus toxin and botulinum serotypes B, D, F, and G cleave synaptobrevin (also called VAMP) [Pellizarri, R., et al. (1999) Philos. Trans. Royal Soc. London B. Biol. Sci. 354: 259–268]. Botulinum serotype C cleaves both syntaxin and SNAP-25 [Foran, P., et al. (1996) Biochemistry 35: 2630–2636]. Only one peptide bond is cleaved by each toxin within its substrate, but this is sufficient to inactivate the mechanism of neurotransmitter release. Toxicity is therefore a consequence of clostridial neurotoxin protease activity.

In view of the widespread applications for clostridial neurotoxins in neurological research and in medicine, and because of the possibilities for use as bioweapons, there is an urgent need for highly sensitive and reproducible assays that can be employed to detect the toxins in potentially contaminated food or environmental samples, to accurately quantify the toxins in research reagents or preparations intended for human clinical use, and in the search for anti-toxin drugs. Because botulinum neurotoxins are proteases, it follows that practical assays for this activity could form the basis for detection, quantification, and drug-screening systems. However, the development of such assays has been hampered by several factors: (1) As noted above, each botulinum neurotoxin will cleave only one peptide bond in a particular protein, raising the possibility that separate assays would be required for each toxin. (2) A considerable body of evidence has been published which indicates that the substrate recognition requirements of clostridial neurotoxin proteases are unusually large, compared to other proteases, and include discontinuous segments of their respective neuronal target proteins. Therefore, one would anticipate that only intact target proteins or very long polypeptides derived therefrom can function as substrates [for review, see Schiavo, G. et al. (1995) In: Clostridial Neurotoxins (C. Montecucco, Ed.) pp 257–274, Springer-Verlag, Berlin]. (3) The clostridial neurotoxin proteases do not hydrolyze short peptides spanning the cleavage sites, and the tertiary structures of the target proteins are critical elements in substrate recognition [Rossetto O. et al. (1994) Nature 372: 415–416; Schiavo, G. et al. (1995) supra; Washbourne, P. et al. (1997) FEBS Lett. 418: 1–5]. (4) Relatively minor changes in substrate structure, such as the replacement of only one amino acid with a similar one, even at some considerable distance from the cleavage site, can result in complete loss of substrate function [Yamasaki, S. et al. (1994) J. Biol. Chem. 269: 12764–12772; Shone and Roberts (1994) Eur. J. Biochem 225: 263–270; Schmidt and Bostian (1997) J. Prot. Chem. 16: 19–26]. Consequently, introduction of non-natural amino acids and/or bulky aromatic or fluorescent groups would be unlikely to result in a functional substrate.

Curently, the most commonly used methods for detecting botulinum toxins in food and for estimating concentrations in preparations for clinical use are the mouse lethality bioassay [Siegel and Metzger (1979) Appl. Environ. Micrbiol. 38: 606–611] and the antibody neutralization test [Siegel (1988) J. Clin. Microbiol. 26: 2351–2356]. Both require the use of animals, can take up to four days to complete, and are inherently inaccurate. Furthermore, determination of botulinum toxin concentration with the mouse bioassay cannot be used to predict pharmacological potency [Pearce, L. B. et al. (1997) Toxicon 35: 1373–1412].

Assays have been published which incorporate neurotoxin protease activity as one aspect of the overall method [Ekong, T. et al. (1997) Microbiology 143: 3337–3347; Wictome, M. et al. (1999) Appl. Environ. Microbiol. 65: 3787–3792; Keller, J. et al. (1999) J. Appl. Toxicol. 19: S13–S17]. Nonetheless, they are essentially immunoassays, because quantitation of results requires the production and use of specialized antibodies, capable of distinguishing between cleaved and uncleaved substrate, or between cleavage product and intact substrate. They have been developed only for botulinum serotypes A and B. They require multiple binding, elution, and washing steps, and are impractical for true high-throughput systems.

Other assays for the proteolytic activities of tetanus toxin and of serotypes A and B botulinum toxins have been reported [Shone, C. et al. (1993) Eur. J. Biochem. 217: 965–971; Cornille, F. et al. (1994) Eur. J. Biochem. 222: 173–181; Schmidt and Bostian (1995) J. Prot. Chem. 14: 703–708; Soleilhac, J.-M. et al. (1996) Anal. Biochem. 241: 120–127]. Although these assays could be adapted to high-throughput formats, they include high pressure liquid chromatography or solid-phase extraction steps, which add significant time, complexity, and expense to the procedures.

Recently, an assay for the proteolytic activity of type B botulinum neurotoxin has been published, which uses a fluoescence resonance energy transfer (FRET) substrate and does not require physical separation of products from reactants [Anne, C. et al. (2001) Analyt. Biochem. 291: 253–261]. The publication describes one substrate, suitable for use with botulinum serotype B only. Because of the extreme specificity of each clostridial neurotoxin for a particular peptide bond in a particular substrate, and the likelihood that structural modifications to any of the substrates will diminish or abolish cleavability (see discussion above), nothing may be inferred from these results with respect to the suitability of similar modifications to the substrates for the other clostridial neurotoxins, or to modifications of type B substrate other than those described in the publication.

An assay for the proteolytic activity of type A botulinum toxin has been described (U.S. Pat. No. 5,965,699) which can be conveniently used to quantitate, standardize, and compare different preparations of this toxin. The method is readily adapted to high-throughput format, to search for compounds that inhibit botulinum protease activity (i.e. potential anti-botulinum drugs). However, the assay requires the addition of a fluorigenic reagent (e.g. fluorescamine, but others are known), which reacts with one of the proteolytic products to yield a fluorescent derivative. Furthermore, in some cases, test samples might contain compounds that react directly with the fluorigenic reagent to yield fluorescent derivatives, interfering with the measurement of botulinum protease activity.

The assays described in this application are specifically designed to overcome or eliminate all of the difficulties and drawbacks described above. In view of the unusually high degree of substrate specificity and the large substrate recognition requirements exhibited by all clostridial neurotoxins (v.s.), the extensive substrate modifications required for the development of the new assays would appear to render success highly unlikely. Nonetheless, practical assays have been developed, useful for a wide range of applications.

SUMMARY

It is one object of this invention to provide substrate peptides suitable for use in fluorescence resonant energy transfer assays (FRET; also known as quenched-signal assays) for the protease activities of clostridial neurotoxins.

It is another object of the present invention to provide substrate peptides suitable for use in solid phase assays for the protease activities of clostridial neurotoxins.

It is another object of this invention to provide methods for the discovery of compounds that inhibit or otherwise modulate clostridial neurotoxin protease activities. Such compounds may be useful in botulinum toxin clinical applications, or as anti-clostridial neurotoxin drugs.

It is another object of this invention to provide methods for determining the concentrations of clostridial neurotoxins in samples (e.g. preparations of toxin intended for human clinical use) or for detecting the presence of BoNTs in food or environmental samples, based on the proteolytic activities of the toxins and utilizing the substrates described herein.

It is another object of this invention to provide methods for detecting the presence of clostridial neurotoxins (in food, environmental samples, etc.), based on the proteolytic activities of the toxins and utilizing the substrates described herein.

BRIEF DESCRIPTION OF THE DRAWINGS

These and other features, aspects, and advantages of the present invention will become better understood with regard to the following description, appended claims, and accompanying drawing.

FIGS. 2a and 2b Fluorescence solublized by different concentrations of botulinum toxins, serotypes A, B, D, and F.

DETAILED DESCRIPTION

Figure 1:
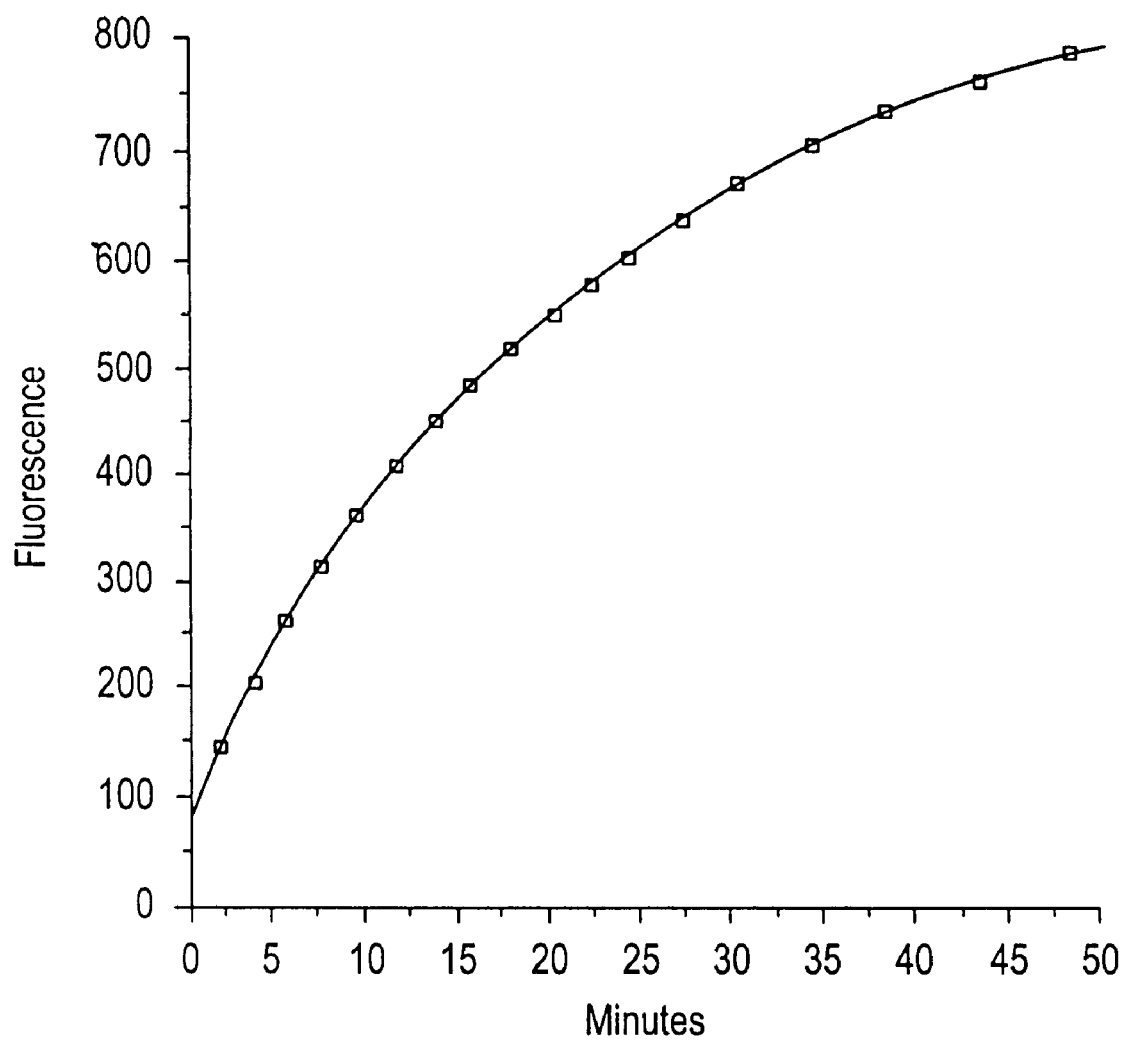
FIG. 1: Hydrolysis of peptide (1) by recombinant type A catalytic domain.
Figure 2A:
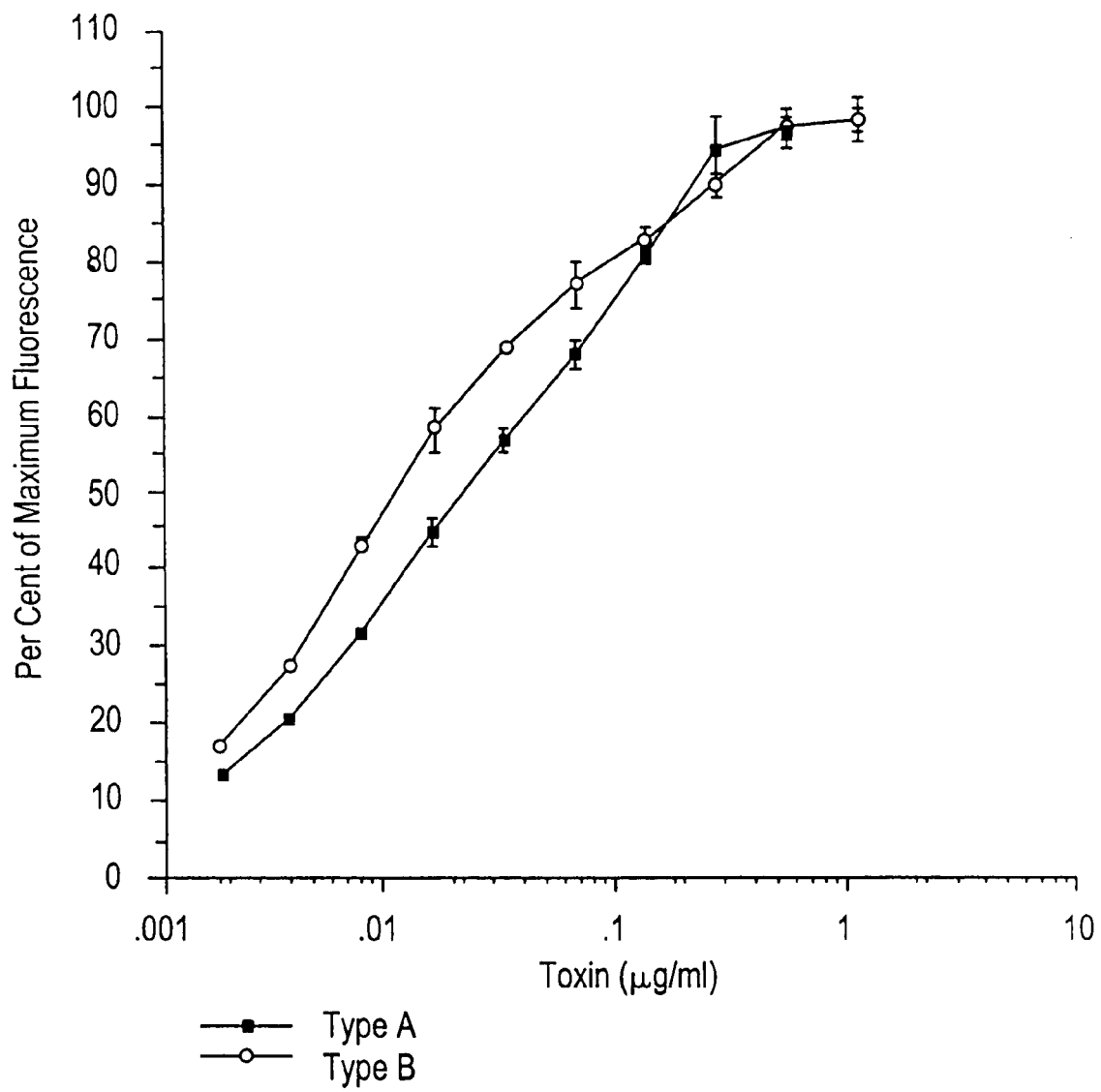

The present invention relates to peptides suitable for the determination of clostridial neurotoxin proteolytic activities. The term "clostridial neurotoxins" refers to the seven serotypes of neurotoxin (types A through G, inclusive) produced by *Clostridium botulinum*, and to tetanus toxin, produced by *Clostridium tetani*.

The invention includes two types of substrates: (I), modified peptides or proteins that can serve as FRET or quenched-signal substrates in assays for the proteolytic activities of clostridial neurotoxins, and (II), modified peptides or proteins that can serve as immobilized substrates (i.e. covalently or otherwise bound to a solid phase) in assays for the proteolytic activities of clostridial neurotoxins. In both types, a fluorescent molecule is present in the substrate, eliminating the requirement for the addition of a fluorigenic reagent. In assays with type (I) substrates, toxin-catalyzed hydrolysis results in a proportional increase in fluorescence. Therefore, physical separation of cleavage products from intact substrate is not necessary. In type (II) assays, separation of products from intact substrate is accomplished by simply transferring all or part of the soluble fraction to another container, followed by quantitation of the fluorescence in the soluble fraction. Circumstances which favor the use of one type of assay over the other are discussed below. The assays are called "high-throughput" because lengthy processing steps such as centrifugation, solid-phase extraction, or chromatography are not needed. Therefore, the assays can be readily adapted for use in automated or robotic systems.

Circumstances favoring the use of one type of assay over the other include:(1), Cost. In some instances, synthesis of a type (I) substrate is more expensive than a type (II) substrate for the same serotype. The substrates for botulinum serotype A described in claims (2) and (9) illustrate this situation. The former, a FRET or type (I) substrate, is more costly to produce than the latter. Therefore, if very large numbers of type A assays are anticipated, economics favors the use of assays incorporating substrate (9), or another type (II) substrate. (2), Available instrumentation. The most efficient use of type (II) substrates is in multiwell arrays. However, a fluorometer capable of reading such arrays is required. If a multiwell fluorometer is not available, use of a FRET substrate would be indicated. (3), Determinations of clostridial protease kinetic constants. Initial rates of substrate hydrolyses, catalyzed by clostridial neurotoxin protease activities, are most conveniently determined using FRET or type (I) substrates. Measurements of initial rates are required for calculations of kinetic constants, such as Km, kcat (turnover number), and the binding affinities of inhibitors or other effectors. (4), Interference of test samples with direct fluorescence measurements. Properties of certain test compounds, such as quenching, turbidity, or fluorescence, might preclude quantitation of assay results by direct fluorescence measurements. In this situation, use of a solid-phase or type (II) assay is indicated. At the conclusion of the incubation period, samples are removed and the wells are washed to remove all test compounds and enzymes. The amount of uncleaved substrate still bound to each well is then determined by incubation with trypsin, 50–100 micrograms per ml, followed by fluorescence measurements. In this situation, the presence of an inhibitor is indicated by a higher fluorescence reading, compared to the control, instead of a lower reading, as in direct assays. (5) Test samples bound to solid matrices. For example, combinatorial chemistry libraries are often attached to resin beads. In this case, use of a FRET substrate is sometimes more convenient than a solid-phase substrate.

Type (I) substrates:

The following are examples of FRET substrates for the proteolytic activities of clostridial neurotoxins. Each contains a fluorescent group (fluorophore) on one side of the cleavage site, and a molecule that quenches that fluorescence on the other side of the cleavage site. Upon neurotoxin-catalyzed hydrolysis, the fluorophore and quencher diffuse away from each other, and the fluorescence signal increases in proportion to the extent of hydrolysis. Therefore, the occurrence and rate of hydrolysis may be determined by following the increase in fluorescence with a suitable fluorimeter. Addition of fluorigenic reagents, transfer or washing steps, or substrate immobilization are not required.

Sequences of type A botulinum protease substrates described in U.S. Pat. No. 5,965,699, all of which can be modified as described below for use as FRET substrates, are herein incorporated by reference.

```
1  2  3  4  5  6  7  8  9  10 11 12 13 14 15 16 17 18 19 20

L  S  E  L  D  D  R  A  D  A  L  Q  A  G  A  S  X  F  E  dcC 21 22 23 24 25 26 27 28 29 30 31 32 33 34 35

S  A  A  K  L  K  R  K  Y  W  W  K  N  L  K
```

Substrate (1) (SEQ ID NO:1) is the following peptide:

```
1  2  3  4  5  6  7  8  9  10 11 12 13 14 15 16 17

S  N  R  T  R  I  D  X  A  N  Q  R  A  Z  R  M  L
```

Where "X" is N(epsilon)-(2,4-dinitrophenyl)-lysine and "Z" is S-(fluoresceinyl)-cysteine. This peptide is a substrate for the proteolytic activity of type A botulinum neurotoxin. Cleavage occurs between residues 11 (Q) and 12 (R).

Substrate (2) (SEQ ID NO:2) is the following peptide:

```
1  2  3  4  5  6  7  8  9  10 11 12 13 14 15 16 17

S  N  R  T  R  I  D  E  A  N  X  R  A  dcC R  M  L
```

Where "X" is N(epsilon)-(2,4-dinitrophenyl)-lysine and "dcC" is S-(7-dimethylamino-4-methyl-coumarin-3-carboxamidomethyl)-cysteine. This peptide is a substrate for the proteolytic activity of type A botulinum neurotoxin. Cleavage occurs between residues 11 (N(epsilon)-(2,4-dinitrophenyl)-lysine) and 12 (R).

Substrate (3)(SEQ ID NO:3) is the following peptide:

```
1  2  3  4  5  6  7  8  9  10 11 12 13 14 15 16 17 18 19 20

L  S  E  L  D  D  R  A  D  A  L  Q  A  X  A  S  Q  F  E  Z 21 22 23 24 25 26 27 28 29 30 31 32 33 34 35

S  A  A  K  L  K  R  K  Y  W  W  K  N  L  K
```

Where "X" is N(epsilon)-(2,4-dinitrophenyl)-lysine and "Z" is S-(fluoresceinyl)-cysteine. This peptide is a substrate for the proteolytic activity of type B botulinum neurotoxin. Cleavage occurs between residues 17 (Q) and 18(F).

Substrate (4) (SEQ ID NO:4) is the following peptide:

Where "X" is N(epsilon)-(2,4-dinitrophenyl)-lysine and "dcC" is S-(7-dimethylamino-4-methyl-coumarin-3-carboxamidomethyl)-cysteine. This peptide is a substrate for the proteolytic activity of type B botulinum neurotoxin. Cleavage occurs between residues 17 (N(epsilon)-(2,4-dinitrophenyl)-lysine) and 18(F).

Substrate (5) (SEQ ID NO:5) is the following peptide:

```
1  2  3  4  5  6  7  8  9  10 11 12 13 14 15 16 17 18 19 20

A  Q  V  D  E  V  V  D  I  M  R  V  N  V  D  K  V  L  X  R 21 22 23 24 25 26 27 28 29 30 31 32 33 34 35 36 37 38

D  Q  K  L  Z  E  L  D  D  R  A  D  A  L  Q  A  G  A

39

S
```

Where "X" is N(epsilon)-(2,4-dinitrophenyl)-lysine and "Z" is S-(fluoresceinyl)-cysteine. This peptide is a substrate for the proteolytic activities of types D and F botulinum neurotoxins. Type D cleaves between residues 23 (K) and 24 (L), while type F cleaves residues 22 (Q) and 23 (K).

Substrate (6) (SEQ ID NO:6) is the following peptide:

```
 1  2  3  4  5  6  7  8  9 10 11 12 13 14 15 16 17 18 19 20
 A  Q  V  D  E  V  V  D  I  M  R  V  N  V  D  K  V  L  E  R 21 22 23 24  25 26 27 28 29 30 31 32 33 34 35 36 37 38
 D  X  K  L  dcC E  L  D  D  R  A  D  A  L  Q  A  G  A

39
 S
```

Where "X" is N(epsilon)-(2,4-dinitrophenyl)-lysine and "dcC" is S-(7-dimethylamino-4-methyl-coumarin-3-carboxamidomethyl)-cysteine. This peptide is a substrate for the proteolytic activities of types D and F botulinum neurotoxins. Type D cleaves between residues 23 (K) and 24 (L). Cleavage by type F occurs between residues 22 (N(epsilon)-(2,4-dinitrophenyl)-lysine) and 23 (K).

Substrate (7) (SEQ ID NO:7) is the following peptide:

```
 1  2  3  4  5  6  7  8  9 10 11 12 13 14 15 16 17 18 19 20
 A  Q  V  D  E  V  V  D  I  M  R  V  N  V  D  K  V  L  E  R 21 22 23 24  25 26 27 28 29 30 31 32 33 34 35 36 37 38
 D  X  K  L  mcp E  L  D  D  R  A  D  A  L  Q  A  G  A

39
 S
```

Where "X" is N(epsilon)-(2,4-dinitrophenyl)-lysine and "mcp" is 2-amino-3-(7-methoxycoumarin-4-yl)-propionic acid. This peptide is a substrate for the proteolytic activities of types D and F botulinum neurotoxins. Type D cleaves between residues 23 (K) and 24 (L). Cleavage by type F occurs between residues 22 (N(epsilon)-(2,4-dinitrophenyl)-lysine) and 23 (K).

Substrate (8):

Any peptide or protein that can serve as a substrate for the proteolytic activity of any clostridial neurotoxin, said protein or peptide having been modified to contain a signal moiety on one side of the cleavage site, and a moiety on the other side of the cleavage site that quenches or diminishes the magnitude of that signal. When the substrate is cleaved by clostridial neurotoxin proteolytic activity, the two diffuse away from each other and the signal increases in proportion to the amount of cleavage that has occurred. Examples of signal and quench moieties include, respectively: coumarin derivatives and N(epsilon)-(2,4-dinitrophenyl)-lysine; coumarin derivatives and nitrotyrosine; fluorescein and rhodamine; fluorescein and N(epsilon)-(2,4-dinitrophenyl)-lysine among others known in the art.

The general concept of FRET assays has been known for many proteases. However, knowledge provided by FRET assays for other proteases cannot be applied directly to the development of FRET substrates for clostridial neurotoxin protease activities, due to the extreme substrate specificities, sensitivities to even minor structural changes in substrates, and the very large substrate recognition requirements of the latter enzymes. In view of these complex and stringent limitations, design of FRET substrates for clostridial neurotoxin protease activities, with respect to types of signal and quench moieties and placement within the substrate sequences, is not obvious.

Type (II) Substrates Claimed:

Peptides described in substrate (9)–(13) are examples of clostridial neurotoxin substrates, intended for immobilization through reaction of the sulfhydryl groups of the C-terminal cysteine residues in the peptides with maleimide groups, the latter covalently bound to the walls of multiwell plates.

Sequences of type A botulinum protease substrates described in U.S. Pat. No. 5,965,699, all of which can be modified as described in this application for use as immobilized substrates, are herein incorporated by reference.

Substrate (9) (SEQ ID NO:8) is the following peptide:

```
 1   2  3  4  5  6  7  8  9 10 11 12 13 14 15 16 17 18 19 20
 flG G  G  S  N  R  T  R  I  D  E  A  N  Q  R  A  T  R  M  L 21 22 23 24
 G  G  G  C
```

Where flG is N-fluoresceinyl-glycine. This peptide is a substrate for the proteolytic activity of type A botulinum neurotoxin. Cleavage occurs between residues 14 (Q) and 15 (R).

Substrate (10) (SEQ ID NO:9) is the following peptide:

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| flG | G | G | L | S | E | L | D | D | R | A | D | A | L | Q | A | G | A | S | Q |

| 21 | 22 | 23 | 24 | 25 | 26 | 27 | 28 | 29 | 30 | 31 | 32 | 33 | 34 | 35 | 36 | 37 | 38 |
|----|----|----|----|----|----|----|----|----|----|----|----|----|----|----|----|----|----|
| F | E | T | S | A | A | K | L | K | R | K | Y | W | W | K | N | L | K |

| 39 | 40 | 41 | 42 |
|----|----|----|----|
| G | G | G | C |

Where flG is N-fluoresceinyl-glycine. This peptide is a substrate for the proteolytic activity of type B botulinum neurotoxin. Cleavage occurs between residues 20 (Q) and 21 (F).

Substrate (11) (SEQ ID NO:10) is the following peptide:

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| flG | G | G | A | Q | V | D | E | V | V | D | I | M | R | V | N | V | D | K | V |

| 21 | 22 | 23 | 24 | 25 | 26 | 27 | 28 | 29 | 30 | 31 | 32 | 33 | 34 | 35 | 36 | 37 | 38 |
|----|----|----|----|----|----|----|----|----|----|----|----|----|----|----|----|----|----|
| L | E | R | D | Q | K | L | S | E | L | D | D | R | A | D | A | L | Q |

| 39 | 40 | 41 | 42 | 43 | 44 | 45 | 46 |
|----|----|----|----|----|----|----|----|
| A | G | A | S | G | G | G | C |

Where flG is N-fluoresceinyl-glycine. This peptide is a substrate for the proteolytic activities of both types D and type F botulinum neurotoxins. With type D, cleavage occurs between residues 26 (K) and 27 (L), while type F catalyzes hydrolysis between residues 25 (Q) and 26(K).

Substrate (12) (SEQ ID NO:11) is the following peptide:

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| Z | N | K | L | K | S | S | D | A | Y | K | K | A | W | G | N | N | Q | D | G |

| 21 | 22 | 23 | 24 | 25 | 26 | 27 | 28 | 29 | 30 | 31 | 32 | 33 | 34 | 35 | 36 | 37 | 38 |
|----|----|----|----|----|----|----|----|----|----|----|----|----|----|----|----|----|----|
| V | V | A | S | Q | P | A | R | V | V | D | E | R | E | Q | M | A | I |

| 39 | 40 | 41 | 42 | 43 | 44 | 45 | 46 | 47 | 48 | 49 | 50 | 51 | 52 | 53 | 54 | 55 | 56 |
|----|----|----|----|----|----|----|----|----|----|----|----|----|----|----|----|----|----|
| S | G | G | F | I | R | R | V | T | N | D | A | R | E | N | E | M | D |

| 57 | 58 | 59 | 60 | 61 | 62 | 63 | 64 | 65 | 66 | 67 | 68 | 69 | 70 | 71 | 72 | 73 | 74 |
|----|----|----|----|----|----|----|----|----|----|----|----|----|----|----|----|----|----|
| E | N | L | E | Q | V | S | G | I | I | G | N | L | R | H | M | A | L |

| 75 | 76 | 77 | 78 | 79 | 80 | 81 | 82 | 83 | 84 | 85 | 86 | 87 | 88 | 89 | 90 | 91 | 92 |
|----|----|----|----|----|----|----|----|----|----|----|----|----|----|----|----|----|----|
| D | M | G | N | E | I | D | T | Q | N | R | Q | I | D | R | I | M | E |

| 93 | 94 | 95 | 96 | 97 | 98 | 99 | 100 | 101 | 102 | 103 | 104 | 105 | 106 | 107 |
|----|----|----|----|----|----|----|-----|-----|-----|-----|-----|-----|-----|-----|
| K | A | D | S | N | K | T | R | I | D | E | A | N | Q | R |

| 108 | 109 | 110 | 111 | 112 | 113 | 114 | 115 | 116 |
|-----|-----|-----|-----|-----|-----|-----|-----|-----|
| A | T | K | M | L | G | S | G | C |

Where Z is S-fluoresceinyl-cysteine. This peptide is a substrate for the proteolytic activities of types A and E botulinum neurotoxins. Type A cleaves between residues 106 (Q) and 107 (R), while type E catalyzes hydrolysis between residues 89 (R) and 90 (I).

Substrate (13) (SEQ ID NO:12) is the following peptide:

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| Z | N | K | L | S | S | D | A | Y | K  | K  | A  | W  | G  | N  | N  | Q  | D  | G  |    |

| 21 | 22 | 23 | 24 | 25 | 26 | 27 | 28 | 29 | 30 | 31 | 32 | 33 | 34 | 35 | 36 | 37 | 38 |
|----|----|----|----|----|----|----|----|----|----|----|----|----|----|----|----|----|----|
| V  | V  | A  | S  | Q  | P  | A  | R  | V  | V  | D  | E  | R  | E  | Q  | M  | A  | I  |

| 39 | 40 | 41 | 42 | 43 | 44 | 45 | 46 | 47 | 48 | 49 | 50 | 51 | 52 | 53 | 54 | 55 | 56 |
|----|----|----|----|----|----|----|----|----|----|----|----|----|----|----|----|----|----|
| S  | G  | G  | F  | I  | R  | R  | V  | T  | N  | D  | A  | R  | E  | N  | E  | M  | D  |

| 57 | 58 | 59 | 60 | 61 | 62 | 63 | 64 | 65 | 66 | 67 | 68 | 69 | 70 | 71 | 72 | 73 | 74 |
|----|----|----|----|----|----|----|----|----|----|----|----|----|----|----|----|----|----|
| E  | N  | L  | E  | Q  | V  | S  | G  | I  | I  | G  | N  | L  | R  | H  | M  | A  | L  |

| 75 | 76 | 77 | 78 | 79 | 80 | 81 | 82 | 83 | 84 | 85 | 86 | 87 | 88 | 89 | 90 | 91 | 92 |
|----|----|----|----|----|----|----|----|----|----|----|----|----|----|----|----|----|----|
| D  | M  | G  | N  | E  | I  | D  | T  | Q  | N  | R  | Q  | I  | D  | R  | I  | M  | E  |

| 93 | 94 | 95 | 96 | 97 | 98 | 99 | 100 | 101 | 102 | 103 | 104 | 105 | 106 | 107 |
|----|----|----|----|----|----|----|-----|-----|-----|-----|-----|-----|-----|-----|
| K  | A  | D  | S  | N  | K  | T  | R   | I   | D   | E   | A   | N   | Q   | A   |

| 108 | 109 | 110 | 111 | 112 | 113 | 114 | 115 | 116 |
|-----|-----|-----|-----|-----|-----|-----|-----|-----|
| A   | T   | K   | M   | L   | G   | S   | G   | C   |

Where Z is S-fluoresceinyl-cysteine. This peptide is a substrate for the proteolytic activity of type E botulinum neurotoxin. Type E catalyzes hydrolysis between residues 89 (R) and 90 (I). Replacement of arginine-107 (see sequence in substrate (12)) with alanine prevents cleavage of this substrate by type A botulinum neurotoxin.

Substrate (14):

Any peptide or protein that can serve as a substrate for the proteolytic activity of any clostridial neurotoxin, said protein or peptide having been modified so that it can be attached on one side of the proteolytic cleavage site to a solid or insoluble material. The attachment point can be on either side (i.e. C-terminal or N-terminal) of the cleavage site. Examples of attachment methods include (but are not limited to): (a), reaction of sulfydryl groups in the substrate peptide molecules with maleimide groups pre-attached to the solid material (or, vice versa); (b), binding of biotin groups in the substrate molecules to avidin or streptavidin groups on the solid material (or, vice versa). Examples of solid materials for use in this context include, but are not limited to: (a) multiwell plastic plates; (b), plastic pins or "dipsticks"; (c), agarose beads, silica beads, plastic beads, or other types of spherical or fibrous chromatographic media; (d), nitrocellulose or other types of sheets or membranes.

On the other side of the cleavage site, opposite from the point of attachment, the substrate contains a moiety that produces a measurable signal, such as, but not limited to, a fluorescent group or a radioactive isotope. When the proteolytic activity of a clostridial neurotoxin cleaves such a substrate, the product containing the signal is released into solution. Subsequently, the amount of signal in the soluble fraction is measured. In addition, if necessary, the amount of residual bound signal can also be measured following solubilization of the latter with a protease such as trypsin.

Immobilized substrate assays have been developed for many types of enzymes, including other proteases. However, the unusually extensive substrate recognition requirements of the clostridial neurotoxins and the relatively large size of the toxin catalytic subunit (i.e. the light chain, Mr ~50,000) argue against the attachment of neurotoxin-specific substrates to solid supports. Such an arrangement would be expected to result in considerable steric hindrance, preventing free access of the toxin to the substrate on all sides. Furthermore, the stringent requirements of clostridial neurotoxins with respect to substrate amino acid sequence indicates that introduction of bulky fluorescent groups or other signal moieties into potential substrates would eliminate functionality. Therefore, application of knowledge gained from earlier immobilized assays for other enzymes to the development of similar assays for clostridial neurotoxin protease activities is not encouraged and is not straightforward.

Abbreviations for the amino acids are:
A Alanine
D Aspartic acid
E Glutamic acid
I Isoleucine
K Lysine
L Leucine
M Methionine
N Asparagine
Q Glutamine
R Arginine
S Serine
T Threonine
X N-epsilon-(2,4 dinitrophenyl) lysine
Z S-(fluoresceinyl)-cysteine
dcC S-(7-dimethylamino-4-methyl-coumarin-3-carboxamidomethyl) cysteine
mcp 2-amino-3-(7-methoxycoumarin-4-yl)-propionic acid
flG N-fluoresceinyl-glycine Peptides can be made with commercially available automated synthesizers, using reagents and protocols obtained from the manufacturers. Amino acids can be obtained in chemically-modified ("protected") forms, designed so that they will react with the free amino group of the preceding residue in the peptide chain, but not with themselves. Upon completion of synthesis, the peptide is cleaved from the resin, protecting groups are removed, and the product is purified. These preparation protocols and others are well within the skill of a person in the art.

In another embodiment, the present invention provides a method for screening compounds which alter BoNT activity, such as inhibitors of BoNT activity or stimulators of BoNT activity. Solutions of BoNT or recombinant botulinum toxin are incubated with each test compound at ambient temperature, transferred to solid supports onto which is immobilized a peptide substrate for the BoNT enzyme being tested as described above, and processed as described above. A toxin incubated with a test compound which exhibits a reduction in the ability of the toxin to cleave the peptide substrate relative to unincubated toxin indicates a inhibitory compound. Alternatively, a toxin incubated with a test compound which exhibits an increase in the ability of the toxin to cleave the peptide substrate relative to unincubated toxin indicated a stimulatory compound.

In another embodiment, the present invention relates to a kit to search for compounds which inhibit or otherwise alter the protease activities of clostridial neurotoxins. Because the biological effects of clostridial neurotoxins are consequences of their protease activities, it follows that compounds which affect these activities might prove useful as anti-toxin drugs or as tools for further toxin research. Examples of compounds that could be tested include combinatorial sets of chemicals, phage display libraries, or arrays of plant extracts. The kit will contain in close confinement, in a box for example:

optionally, one or more underivatized multiwell plates ("preincubation plates");

an equal number of derivatized multiwell substrate plates, which contain substrates for clostridial neurotoxin protease activities bound to the walls of the wells. In most cases, a well will contain substrate for only one clostridial neurotoxin serotype, but combinations of substrates may be used;

optionally, an equal number of opaque-wall multiwell plates, suitable for use in a multiwell fluorimeter;

one or more of the clostridial neurotoxins or recombinant light chains thereof;

optionally dry buffer components.

Solutions of neurotoxin or light chain in buffer are mixed with test compounds in the same buffer in preincubation plate wells and incubated at ambient temperature for approximately 15–30 min. This step allows the compounds to exert effects, if any, on the toxins before exposure to the substrates. As controls, wells containing toxin or light chain without test compounds are included. Following preincubation, the solutions are transferred to wells in the derivatized plates containing immobilized fluorescent substrate specific for the clostridial neurotoxin being tested. For example, if type A botulinum neurotoxin is tested, then wells could contain the peptide described in substrate (9). Substrate plates are incubated for 1–3 hours at 30°–37° C. During this time, the toxin or light chain protease activity will cleave the immobilized substrate to a certain extent, thereby solublizing the proteolysis product containing the fluorescent group. Solutions are then transferred to the corresponding wells of opaque-wall plates. Fluorescence is then quantitated in a multiwell fluorimeter. Wells containing compounds that stimulated or inhibited toxin protease activity will have more or less fluorescence, respectively, compared to control wells containing toxin only.

In another embodiment, the present invention relates to a kit for determining the concentrations of clostridial neurotoxins in samples; for example, it may be used to monitor the various stages of botulinum toxin production, intended for human clinical applications. Use of this kit requires knowledge of which botulinum serotype is present, and the absence of interfering protease(s). If these conditions are not met, use of the third kit described below is indicated. For illustrative purposes, a kit is described for determining concentrations of type A botulinum neurotoxin. The kit will contain in close confinement, in a box for example:

FRET substrate for type A botulinum neurotoxin, described in substrate (2), dry;

optionally, dry buffer components;

optionally, tween-20 detergent;

type A botulinum neurotoxin standard.

A solution of 30 micromolar substrate is prepared in water, buffered at pH 7.3 and containing 0.05% v/v tween-20. Solutions of various known concentrations of type A botulinum neurotoxin are prepared in the same buffer. Toxin is mixed with substrate, the increase in fluorescence is measured for a period of time, and the initial rate of fluorescence increase is determined from the early (essentially linear) part of the curve. This is repeated for each known concentration of toxin, establishing a correlation between toxin concentration and rate. Cleavage rates are then determined for samples containing unknown concentrations of type A neurotoxin. By comparison with the standards, the unknown concentrations may be calculated.

In another embodiment, the present invention relates to a kit for detecting the presence of clostridial neurotoxins in samples. In addition to detection, the kit will also eliminate interfering proteases that might be present, identify the serotypes of the neurotoxins, and permit calculations of neurotoxin concentrations. Kits may be used to screen just a few samples, or large numbers of samples at once. The kit will contain in close confinement, in a box for example:

a multiwell plate, containing biotinylated antibodies against all serotypes of the clostridial neurotoxins, bound to avidin- or streptavidin-coated wells. The antibodies are specific for the heavy chains of the toxins. Generally, a particular well would contain antibodies against only one of the clostridial neurotoxins, but all would be represented on the plate. However, in cases where volume of test sample is limited, wells could contain more than one type of antibody. The plate is preferably suitable for use in a multiwell fluorimeter;

optionally, dry buffer components for wash buffer;

optionally, dry activation buffer components, containing buffer, dithiothreitol, and zinc chloride;

optionally, Tween-20 detergent;

Clostridial neurotoxin standards.

Type (I) FRET substrates and/or type (II) substrates, the latter preferably immobilized, for example, by attachment to derivatized plastic pins which are commercially available. The pins can be used individually, or may be attached to plate lids in an array that corresponds to that of the plate wells, such that, when a lid is applied to a plate, one pin enters each well.

Solutions of samples suspected of containing clostridial neurotoxins are placed in plate wells. Wells containing antibodies against each clostridial neurotoxin should receive sample, but if sample volume is limited, wells containing multiple anti-neurotoxin antibodies would be used. Plates are incubated for approximately one hour at 30°–37° C. During this time, clostridial neurotoxins, if present, will bind to the anti-toxin antibodies in the wells. Wells are then washed with wash buffer (typically, 50 mM tris, 0.1% v/v tween-20, pH 7.5, but others may be used) to remove unbound components including, if present, proteases other than the clostridial neurotoxins. Activation solution (20 mM buffer, 10 mM dithiothreitol, 0.50 mM zinc chloride. pH 7.3) is added and incubated at 30°–37° C. for 20–30 minutes to activate clostridial neurotoxin protease activities. Solutions containing FRET substrates are added, corresponding to the type of neurotoxin that would be captured by the antibody in a particular well. After one hour incubation at 30°–37° C., the amounts of fluorescence in the wells are determined with a fluorimeter. By comparing fluorescence readings in test sample wells to those obtained from control wells (buffers and substrates only) and to readings from wells containing neurotoxin standards, the presence of a clostridial neurotoxin in a sample may be detected, and its concentration determined. By noting the specificity of the antibody in a positive well, the serotype of the clostridial neurotoxin is revealed.

Alternatively, plastic pins derivatized with the appropriate type (II) immobilized substrates are placed in the wells, instead of type (I) FRET substrates. (Circumstances favoring the use of one substrate type over the other are discussed in a preceding section). After incubation, the pins are removed. If the pins were arrayed in a plate lid, corresponding to the well array, this is accomplished simply by removing the lid. The amount of fluorescence in the wells is then determined in a multiwell fluorimeter. Calculations of results are done as discussed above.

In situations where wells containing antibodies against more than one serotype must be used, differentiation among neurotoxin serotypes is enabled by using substrates containing different fluorophores. For example, a well might contain antibodies against botulinum serotypes A, B, E, and F. After incubation of sample, washing, and activation, a multi-substrate plastic pin with a combination of four immobilized type (II) substrates is placed in the well. In this example, the pin is derivatized with: (1) substrate for botulinum type A described in substrate (9); (2) substrate for botulinum type B described in substrate (10), modified to replace N-fluoresceinyl-glycine with N-rhodaminyl-glycine as the N-terminal moiety; (3) substrate for botulinum type E described in substrate (13), modified to replace S-fluoresceinyl-cysteine with N-(7-methoxy-coumarin-4-acetyl)-glycine as the N-terminal moiety; (4) substrate for botulinum type F described in substrate (11), modified to replace N-fluoresceinyl-glycine with S-(4-acetamido-stilbene-2-2'-disulfonic acid-4'-carboxamidomethyl)-cysteine. Because the four fluorophores have distinct and well-separated emission spectra, the presence of one or more botulinum serotype(s) is/are revealed by determining the wavelength(s) of any fluorescence remaining in the well after the removal of the plastic pin.

Immobilization of clostridial neurotoxin serotype-specific antibodies may be accomplished in other ways. For example, instead of substrates, the antibodies are bound to plastic pins or dipsticks, for use either individually or in arrays corresponding to multiwell plates. The pins are immersed in test samples. If clostridial neurotoxins are present, they will be captured by the antibodies. After rinsing, the pins are immersed in solutions containing activation buffer (see above), followed by addition of type (I) FRET substrates. An increase in fluorescence (compared to appropriate controls) indicates the presence of neurotoxin. The serotype is revealed by the type of antibody on the pin. The concentration may be calculated from a standard curve constructed with known concentrations of neurotoxin.

Alternatively, plastic pins derivatized with the appropriate type (II) immobilized substrates are placed in the wells, instead of type (I) FRET substrates. (Circumstances favoring the use of one substrate type over the other are discussed in a preceding section). After incubation (v.s.), the pins are removed. If the pins were arrayed in a plate lid, corresponding to the well array, this is accomplished simply by removing the lid. The amount of fluorescence in the wells is then determined in a multiwell fluorimeter. Calculations of results are done and conclusions drawn as discussed above.

In another modification, neurotoxin-specific antibodies are bound to the surface of a sheet or membrane in roughly circular spots, corresponding to a multiwell plate array. The sheet or membrane is immersed in the test sample, followed by rinsing. The sheet is then clamped between the upper and lower halves of a multiwell plate, such that the sheet forms the bottom of each well. Alternatively, instead of immersing the sheet in the sample, test samples may be added to the wells, then washed out, or removed by drawing through the sheet by application of a vacuum to the lower plate half. Activation buffer and then type (I) FRET substrates are added to the wells. Results are calculated and conclusions drawn as noted above. Multiwell plates consisting of separable upper and lower halves or chambers, with and without the capability of applying vacuum to the lower chamber, are commercially available and not specifically claimed in this patent application.

The following examples are illustrative of the practice of the invention but should not be read as limiting the scope thereof. It is understood that various modifications could be suggested within the spirit and purview of this application and the scope of the claims.

The following materials and methods were used in the examples below.

Materials and Methods

Enzyme Preparations

Botulinum toxins were obtained from Food Research Institute, Madison, Wis. All preparations appeared to be more than 90% pure, as judged by SDS-PAGE under reducing conditions. Botulinum toxins were used only by immune personnel under Biosafety Level-2 controls, in accordance with the recommendations of the U.S. Centers for Disease Control and Prevention [*Biosafety in Microbiological and Biomedical Laboratories* (1999) U.S. Government Printing Office, Washington, D.C.]. Maleimide-activated 96-well plates were purchased from Pierce Chemical Co., Rockford, Ill.

Recombinant botulinum type A light chain was expressed in competent *E. coli* BL21 cells (Stratagene, La Jolla, Calif.) using a synthetic gene [Ahmed and Smith (2000) *J. Prot. Chem.* 19: 475–487] and a pET vector based upon the T7 RNA polymerase expression system Studier et al. (1990) *Methods Enzymol.* 185: 60–89]. Soluble recombinant type A light chain was purified to >90% purity by ion exchange chromatography at room temperature [Li and Singh (1999) *Prot Expr. Purif.* 17: 339–344]. 12:31 PM Peptide Synthesis The peptide synthesizer was a model 431A from Perkin Elmer-Applied Biosystems, Foster City, Calif. We used protocols, reagents, and chemicals obtained from the manufacturer. Rink resin was employed to yield a carboxamide at the C-terminal residues of all peptides. N(alpha)-FMOC-N(epsilon)-2,4-dnitrophenyl-lysine and N-FMOC-2-amino-3 (7-methoxycoumarin-4-yl)-propionic acid were purchased from Bachem Bioscience, King of Prussia, Pa.

Substrates with S-fluresceinyl cysteine were prepared by reacting the cysteine sulfhydryl group in the substrate with iodoacetamidofluorescein (Pierce Chemical Co., Rockford Ill.). Similarly, substrates containing S-(7-dimethylamino-4-methyl-coumarin-3-carboxamidomethyl)-cysteine were prepared by reaction of the cysteine sulfhydryl group with N-(7-dimethylamino-4-methylcoumarin-3-yl)iodoacetamide (Molecular Probes, Eugene Oreg.).

Fluorescein was coupled to N-terminal glycine by deblocking the alpha-amino group, followed by reacting the resin-bound protected peptide with 5-carboxyfluorescein-N-hydroxysuccinimide ester (Pierce Chemical Co., Rockford, Ill.). Alternatively, 5-carboxy-fluorescein (Aldrich Chemical Co., Milwaukee, Wis.) was loaded into synthesizer cartridges and placed on the instrument as the last residue. Two couplings were required for complete reaction. After deprotection and cleavage from the resins, crude peptides were purified by reverse-phase HPLC.

Preparation of Immobilized-Substrate Assay Plates

For covalent coupling to maleimide-activated multiwell plates, fluorescent peptides were dissolved at concentrations of 15 to 20 μM in 50 mM Tris, 5 mM EDTA, 0.1% tween, pH 7.9. All wells received 100 μL of peptide solution, followed by incubation at ambient temperature for 4–5 h. Wells were emptied, then incubated in succession (200 μL per well, 1 h) with 40 mM 2-mercaptoethanol in Tris-EDTA-tween, then 10 mg/ml BSA in Tris-tween (no EDTA). Finally, wells were washed three times with 200 μL of Tris-tween. Assay plates were stored dry at −10° to −20° C.

Coupling of Substrates to Derivatized Plastic Pins

Derivatized pins (also called "gears") can be obtained from Mimotopes, Raleigh N.C., with N-FMOC-beta-alanine bound through a spacer moiety to the polymer backbone. After removal of the FMOC with piperidine, the free amino group of the beta-alanine is iodoacetylated by reaction with iodoacetic anhydride. Substrate peptide is then covalently bound by reaction of the sulfhydryl group in the substrate cysteine residue with N-iodoacetyl-beta-alanine on the pins.

Assays of Botulinum Toxin Proteolytic Activity

Botulinum toxins (10–20 μg/ml) were preactivated by incubation at 37° C. for 30 min in 20 mM hepes, pH 7.3, 10 mM DTT, 0.50 mM $ZnCl_2$, and 0.05% tween. Assays were conducted in 20 mM hepes, 5 mM DTT, 0.25 mM $ZnCl_2$, and 0.05% tween, with various concentrations of toxins.

When recombinant type A light chain was employed in the assays, the lyophilized enzyme was reconstituted to 35–50 ug/ml with 40 mM hepes/0.05% tween, pH 7.3, followed by dilution to the desired concentraion in the same buffer. Unlike whole toxin, preactivation of light chain is not necessary. Botulinum toxin or recombinant type A light chain were incubated in the substrate-coated plates for varying times at 35° C. in the dark without agitation. Appropriate control wells containing buffer only were included on each plate. Because the maleimide-activated plates have clear walls, they are not optimized for direct fluorescence measurements. Therefore, after incubation, aliquots were transferred to corresponding wells of opaque-wall plates, and fluorescence was measured with a Wallac 1420 multiwell fluorimeter (PerkinElmer Wallac, Gaithersburg Md., USA). Excitation and emission wavelengths were 485 and 535 nm, respectively, with readings of 1 second per well. All fluorescence values were expressed in arbitrary units as the mean of triplicate determinations. Error bars are standard deviations.

Assays employing FRET substrates were done in cuvettes in a temperature-controlled fluorimeter (Photon Technology International, Newtown, Pa.). Toxin or light chain was mixed with appropriate FRET substrate, placed in the instrument, and fluorescence was measured for various times.

EXAMPLE 1

Operation of the Invention Using a Type (I) Substrate:

In this case, the substrate was the peptide described in substrate (1) above, and the enzyme was a recombinant preparation of type A botulinum toxin catalytic domain (also known as "type A light chain"). A solution of 30 micromolar peptide was prepared in water, buffered at pH 7.3, and containing 0.05% v/v tween-20. Before addition of enzyme, fluorescence was measured to obtain the background or "zero-time" fluorescence. Enzyme was then added to a concentration of two micrograms per ml, and the resulting increase in fluorescence due to proteolysis of the peptide was measured with time. Assay temperature was 21° C. In the absence of enzyme, fluorescence changed very little with time, less than ±5%. Results are shown in FIG. 1. The initial rate of hydrolysis can be calculated from the slope of the line in the early (essentially linear) part of the curve. Using known concentrations of toxin or light chain, a correlation between rate and concentration can be established, allowing calculation of toxin or light chain concentrations in unknown samples.

EXAMPLE 2

Operation of the Invention Using Type (II) Substrates:

In this example, the substrates were the peptides described in substrate (9) for botulinum type A, substrate (10) for type B, and substrate (11) for types D and F. The "solid material" to which the substrates were immobilized were 96-well microtiter plates that were chemically modified to contain maleimide groups (see "Materials and methods" section). FIG. 2 depicts fluorescence solubilized by different concentrations of botulinum toxins, serotypes A, B, D, and F (3 hours, 35° C.). For each serotype, maximum fluorescence was defined as that solubilized by 1 microgram per ml toxin under these conditions. The Y-axis extends above 100% to accomodate 12:31 PM the error bars. Panel (a) shows BoNT A and B; panel (b) shows BoNT D and F.

It is understood that these descriptions, examples and embodiments are for illustrative purposes only, and that various modifications would be suggested within the spirit and purview of this application and the scope of the appended claims.

What is claimed is:

1. A botulinum neurotoxin serotype B or tetanus toxin substrate containing a fluorescent signal moiety on one side of the cleavage site that produces a fluorescent signal and a moiety that quenches the magnitude of said signal on the other side of the cleavage site such that when the substrate is cleaved, an increase in fluorescent signal is produced, wherein said substrate is a peptide identified as SEQ ID NO:3 or SEQ ID NO:4.

2. A kit for determining the concentration of botulinum neurotoxin serotype B or tetanus toxin in a sample, the kit containing in close confinement:
   (i) one or both peptide substrates according to claim 1 cleavable by said botulinum neurotoxin or said tetanus toxin; and
   (ii) said botulinum neurotoxin standard or said tetanus toxin standard.

3. A method for measuring the concentration of botulinum neurotoxin serotype B or tetanus neurotoxin in a sample, said method comprising:
   mixing the sample with a peptide substrate identified as SEQ ID NO:3 or SEQ ID NO:4,
   measuring an increase in fluorescent signal with time produced from proteolytic cleavage of said substrate, and
   determining the concentration of said neurotoxin by correlating to a standard of said neurotoxin.

4. A method for detecting the presence of botulinum neurotoxin serotype B or tetanus toxin proteolytic activity in a sample, said method comprising:
   mixing the sample with a peptide substrates identified as SEQ ID NO:3 or SEQ ID NO:4, and
   detecting an increase in fluorescent signal produced from proteolytic cleavage of said substrate.

5. A botulinum neurotoxin serotype B or tetanus toxin substrate comprising a peptide which is optionally immobilized to a solid material and which contains a fluorescent moiety that produces a measurable fluorescent signal such that when the substrate is cleaved, the fluorescent signal is released, wherein said substrate is a peptide identified as SEQ ID NO:9.

6. A kit for determining the concentration of botulinum neurotoxin serotype B or tetanus toxin in a sample, the kit containing in close confinement:
   (i) the peptide substrate according to claim 5 cleavable by said botulinum neurotoxin or said tetanus toxin; and
   (ii) said botulinum neurotoxin or said tetanus toxin standard.

7. A method for detecting the presence of botulinum neurotoxin serotype B or tetanus toxin proteolytic activity in a sample, said method comprising:
   mixing the sample with a peptide substrate identified as SEQ ID NO:9, and
   detecting an increase in fluorescent signal produced from proteolytic cleavage of said substrate.

8. A method for measuring the concentration of botulinum neurotoxin serotype B or tetanus toxin in a sample, said method comprising:
   mixing the sample with a peptide substrate identified as SEQ ID NO:9,
   measuring an increase in fluorescent signal with time produced from proteolytic cleavage of said substrate, and
   determining the concentration of said neurotoxin by correlating to a standard of said neurotoxin.

9. A method for identifying a compound that inhibits or enhances the proteolytic activity of botulinum neurotoxin serotype B or tetanus neurotoxin, said method comprising:
   preincubating the neurotoxin with a test compound to make a neurotoxin-compound solution,
   exposing said solution to a peptide substrate identified as SEQ ID NO:9,
   measuring fluorescent signal resulting from proteolytic cleavage of said substrate by said neurotoxin, and
   comparing said fluorescent signal of the neurotoxin-compound solution with a control,
   wherein the control is the neurotoxin solution without the presence of the test compound, and wherein an increase in fluorescent signal indicates a compound that enhances neurotoxin activity and a decrease in fluorescent signal indicates a compound that inhibits said neurotoxin.

* * * * *

SEQUENCE LISTING

```
<160> NUMBER OF SEQ ID NOS: 12

<210> SEQ ID NO 1
<211> LENGTH: 17
<212> TYPE: PRT
<213> ORGANISM: Artificial sequence
<220> FEATURE:
```

<223> OTHER INFORMATION: synthetic peptide chosen such that it is
                       cleaved by BoNT A
<220> FEATURE:
<221> NAME/KEY: misc_feature
<222> LOCATION: 8 and 14
<223> OTHER INFORMATION: Xaa at 8 is N(epsilon)-2,4-(dinitrophenyl)-
                       lysine and Xaa at 14 is S-(fluresceinyl)-
                       cysteine

<400> SEQUENCE: 1

Ser Asn Arg Thr Arg Ile Asp Xaa Ala Asn Gln Arg Ala Xaa Arg
1               5                  10                  15

Met Leu

<210> SEQ ID NO 2
<211> LENGTH: 17
<212> TYPE: PRT
<213> ORGANISM: Artificial sequence
<220> FEATURE:
<223> OTHER INFORMATION: synthetic peptide chosen such that it is
                       cleaved by BoNT A
<220> FEATURE:
<221> NAME/KEY: misc_feature
<222> LOCATION: 11 and 14
<223> OTHER INFORMATION: Xaa at 11 is N(epsilon)-2,4-(dinitrophenyl)-
                       lysine and Xaa at 14 is S-(7-dimethylamino-4-
                       methyl-coumarin-3-carboxamidomethyl)-cysteine

<400> SEQUENCE: 2

Ser Asn Arg Thr Arg Ile Asp Glu Ala Asn Xaa Arg Ala Xaa Arg
1               5                  10                  15

Met Leu

<210> SEQ ID NO 3
<211> LENGTH: 35
<212> TYPE: PRT
<213> ORGANISM: Artificial sequence
<220> FEATURE:
<223> OTHER INFORMATION: synthetic peptide chosen such that it is
                       cleaved by BoNT B
<220> FEATURE:
<221> NAME/KEY: misc_feature
<222> LOCATION: 14 and 20
<223> OTHER INFORMATION: Xaa at 14 is N(epsilon)-2,4-(dinitrophenyl)-
                       lysine and Xaa at 20 is S-(fluresceinyl)-
                       cysteine

<400> SEQUENCE: 3

Leu Ser Glu Leu Asp Asp Arg Ala Asp Ala Leu Gln Ala Xaa Ala
1               5                  10                  15

Ser Gln Phe Glu Xaa Ser Ala Ala Lys Leu Lys Arg Lys Tyr Trp
                20                  25                  30

Trp Lys Asn Leu Lys
                35

<210> SEQ ID NO 4
<211> LENGTH: 35
<212> TYPE: PRT
<213> ORGANISM: Artificial sequence
<220> FEATURE:
<223> OTHER INFORMATION: synthetic peptide chosen such that it is
                       cleaved by BoNT B
<220> FEATURE:
<221> NAME/KEY: misc_feature
<222> LOCATION: 17 and 20
<223> OTHER INFORMATION: Xaa at 17 is N(epsilon)-2,4-(dinitrophenyl)-
                       lysine and Xaa at 20 is S-(7-dimethylamino-4-
                       methyl-coumarin-3-carboxamidomethyl)-cysteine

```
<400> SEQUENCE: 4

Leu Ser Glu Leu Asp Asp Arg Ala Asp Ala Leu Gln Ala Gly Ala
1               5                   10                  15

Ser Xaa Phe Glu Xaa Ser Ala Ala Lys leu Lys Arg Lys Tyr Trp
            20                  25                  30

Trp Lys Asn Leu Lys
                35

<210> SEQ ID NO 5
<211> LENGTH: 39
<212> TYPE: PRT
<213> ORGANISM: Artificial sequence
<220> FEATURE:
<223> OTHER INFORMATION: synthetic peptide chosen such that it is
                        cleaved by BoNT D or BoNT F
<220> FEATURE:
<221> NAME/KEY: misc_feature
<222> LOCATION: 19 and 25
<223> OTHER INFORMATION: Xaa at 19 is N(epsilon)-2,4-(dinitrophenyl)-
                        lysine and Xaa at 25 is S-(fluresceinyl)-
                        cysteine

<400> SEQUENCE: 5

Ala Gln Val Asp Glu Val Val Asp Ile Met Arg Val Asn Val Asp
1               5                   10                  15

Lys Val Leu Xaa Arg Asp Gln Lys Leu Xaa Glu Leu Asp Asp Arg
            20                  25                  30

Ala Asp Ala Leu Gln Ala Gly Ala Ser
                35

<210> SEQ ID NO 6
<211> LENGTH: 39
<212> TYPE: PRT
<213> ORGANISM: Artificial sequence
<220> FEATURE:
<223> OTHER INFORMATION: synthetic peptide chosen such that it is
                        cleaved by BoNT D or BoNT F
<220> FEATURE:
<221> NAME/KEY: misc_feature
<222> LOCATION: 22 and 25
<223> OTHER INFORMATION: Xaa at 22 is N(epsilon)-2,4-(dinitrophenyl)-
                        lysine and Xaa at 25 is S-(7-dimethylamino-4-
                        methyl-coumarin-3-carboxamidomethyl)-cysteine

<400> SEQUENCE: 6

Ala Gln Val Asp Glu Val Val Asp Ile Met Arg Val Asn Val Asp
1               5                   10                  15

Lys Val Leu Glu Arg Asp Xaa Lys Leu Xaa Glu Leu Asp Asp Arg
            20                  25                  30

Ala Asp Ala Leu Gln Ala Gly Ala Ser
                35

<210> SEQ ID NO 7
<211> LENGTH: 39
<212> TYPE: PRT
<213> ORGANISM: Artificial sequence
<220> FEATURE:
<223> OTHER INFORMATION: synthetic peptide chosen such that it is
                        cleaved by BoNT D or BoNT F
<220> FEATURE:
<221> NAME/KEY: misc_feature
<222> LOCATION: 22 and 25
<223> OTHER INFORMATION: Xaa at 22 is N(epsilon)-2,4-(dinitrophenyl)-
                        lysine and Xaa at 25 is 2-amino-3-(7-
                        methoxycoumarin-4-yl)-propionic acid

<400> SEQUENCE: 7
```

```
Ala Gln Val Asp Glu Val Val Asp Ile Met Arg Val Asn Val Asp
1               5                   10                  15

Lys Val Leu Glu Arg Asp Xaa Lys Leu Xaa Glu Leu Asp Asp Arg
            20                  25                  30

Ala Asp Ala Leu Gln Ala Gly Ala Ser
                35
```

```
<210> SEQ ID NO 8
<211> LENGTH: 24
<212> TYPE: PRT
<213> ORGANISM: Artificial sequence
<220> FEATURE:
<223> OTHER INFORMATION: synthetic peptide chosen such that it is
      cleaved by BoNT A
<220> FEATURE:
<221> NAME/KEY: misc_feature
<222> LOCATION: 1
<223> OTHER INFORMATION: Xaa at 1 is N-fluresceinyl-glycine

<400> SEQUENCE: 8

Xaa Gly Gly Ser Asn Arg Thr Arg Ile Asp Glu Ala Asn Gln Arg
1               5                   10                  15

Ala Thr Arg Met Leu Gly Gly Gly Cys
                20
```

```
<210> SEQ ID NO 9
<211> LENGTH: 42
<212> TYPE: PRT
<213> ORGANISM: Artificial sequence
<220> FEATURE:
<223> OTHER INFORMATION: synthetic peptide chosen such that it is
      cleaved by BoNT B
<220> FEATURE:
<221> NAME/KEY: misc_feature
<222> LOCATION: 1
<223> OTHER INFORMATION: Xaa at 1 is N-fluresceinyl-glycine

<400> SEQUENCE: 9

Xaa Gly Gly Leu Ser Glu Leu Asp Asp Arg Ala Asp Ala Leu Gln
1               5                   10                  15

Ala Gly Ala Ser Gln Phe Glu Thr Ser Ala Ala Lys Leu Lys Arg
                20                  25                  30

Lys Tyr Trp Trp Lys Asn Leu Lys Gly Gly Gly Cys
                35                  40
```

```
<210> SEQ ID NO 10
<211> LENGTH: 46
<212> TYPE: PRT
<213> ORGANISM: Artificial sequence
<220> FEATURE:
<223> OTHER INFORMATION: synthetic peptide chosen such that it is
      cleaved by BoNT D or BoNT F
<220> FEATURE:
<221> NAME/KEY: misc_feature
<222> LOCATION: 1
<223> OTHER INFORMATION: Xaa at 1 is N-fluresceinyl-glycine

<400> SEQUENCE: 10

Xaa Gly Gly Ala Gln Val Asp Glu Val Val Asp Ile Met Arg Val
1               5                   10                  15

Asn Val Asp Lys Val Leu Glu Arg Asp Gln Lys leu Ser Glu Leu
                20                  25                  30

Asp Asp Arg Ala Asp Ala Leu Gln Ala Gly Ala Ser Gly Gly Gly
                35                  40                  45
```

Cys

<210> SEQ ID NO 11
<211> LENGTH: 116
<212> TYPE: PRT
<213> ORGANISM: Artificial sequence
<220> FEATURE:
<223> OTHER INFORMATION: synthetic peptide chosen such that it is
      cleaved by BoNT E
<220> FEATURE:
<221> NAME/KEY: misc_feature
<222> LOCATION: 1
<223> OTHER INFORMATION: Xaa at 1 is S-fluoresceinyl-cysteine

<400> SEQUENCE: 11

```
Xaa Asn Lys Leu Lys Ser Ser Asp Ala Tyr Lys Lys Ala Trp Gly
 1               5                  10                  15

Asn Asn Gln Asp Gly Val Val Ala Ser Gln Pro Ala Arg Val Val
             20                  25                  30

Asp Glu Arg Glu Gln Met Ala Ile Ser Gly Gly Phe Ile Arg Arg
             35                  40                  45

Val Thr Asn Asp Ala Arg Glu Asn Glu Met Asp Glu Asn Leu Glu
             50                  55                  60

Gln Val Ser Gly Ile Ile Gly Asn Leu Arg His Met Ala Leu Asp
             65                  70                  75

Met Gly Asn Glu Ile Asp Thr Gln Asn Arg Gln Ile Asp Arg Ile
             80                  85                  90

Met Glu Lys Ala Asp Ser Asn Lys Thr Arg Ile Asp Glu Ala Asn
             95                 100                 105

Gln Arg Ala Thr Lys Met Leu Gly Ser Gly Cys
            110                 115
```

<210> SEQ ID NO 12
<211> LENGTH: 116
<212> TYPE: PRT
<213> ORGANISM: Artificial sequence
<220> FEATURE:
<223> OTHER INFORMATION: synthetic peptide chosen such that it is
      cleaved by BoNT E
<220> FEATURE:
<221> NAME/KEY: misc_feature
<222> LOCATION: 1
<223> OTHER INFORMATION: Xaa at 1 is S-fluoresceinyl-cysteine

<400> SEQUENCE: 12

```
Xaa Asn Lys Leu Lys Ser Ser Asp Ala Tyr Lys Lys Ala Trp Gly
 1               5                  10                  15

Asn Asn Gln Asp Gly Val Val Ala Ser Gln Pro Ala Arg Val Val
             20                  25                  30

Asp Glu Arg Glu Gln Met Ala Ile Ser Gly Gly Phe Ile Arg Arg
             35                  40                  45

Val Thr Asn Asp Ala Arg Glu Asn Glu Met Asp Glu Asn Leu Glu
             50                  55                  60

Gln Val Ser Gly Ile Ile Gly Asn Leu Arg His Met Ala Leu Asp
             65                  70                  75

Met Gly Asn Glu Ile Asp Thr Gln Asn Arg Gln Ile Asp Arg Ile
             80                  85                  90

Met Glu Lys Ala Asp Ser Asn Lys Thr Arg Ile Asp Glu Ala Asn
             95                 100                 105
```

```
Gln Ala Ala Thr Lys Met Leu Gly Ser Gly Cys
                110                 115
```